United States Patent
Siegel et al.

(10) Patent No.: US 11,744,787 B2
(45) Date of Patent: Sep. 5, 2023

(54) MENTHOL-CONTAINING AROMA PREPARATIONS

(71) Applicants: Symrise AG, Holxminden (DE); Sven Siegel, Höxter (DE)

(72) Inventors: Sven Siegel, Höxter (DE); Arnold Machinek, Holzminden (DE); Benoit Join, Holzminden (DE)

(73) Assignee: Symrise AG, Holxminden (DE)

( * ) Notice: Subject to any disclaimer, the term of this patent is extended or adjusted under 35 U.S.C. 154(b) by 0 days.

(21) Appl. No.: 16/301,233

(22) PCT Filed: May 14, 2016

(86) PCT No.: PCT/EP2016/060932
§ 371 (c)(1),
(2) Date: Nov. 13, 2018

(87) PCT Pub. No.: WO2017/198284
PCT Pub. Date: Nov. 23, 2017

(65) Prior Publication Data
US 2019/0282477 A1    Sep. 19, 2019

(51) Int. Cl.
| | | |
|---|---|---|
| *A61K 8/37* | (2006.01) |
| *A61K 31/05* | (2006.01) |
| *A61K 31/222* | (2006.01) |
| *A61K 8/34* | (2006.01) |
| *A61K 9/68* | (2006.01) |
| *A61K 31/085* | (2006.01) |
| *A61Q 11/00* | (2006.01) |
| *A61K 31/045* | (2006.01) |

(52) U.S. Cl.
CPC ............... *A61K 8/37* (2013.01); *A61K 8/34* (2013.01); *A61K 8/347* (2013.01); *A61K 9/0058* (2013.01); *A61K 31/045* (2013.01); *A61K 31/05* (2013.01); *A61K 31/085* (2013.01); *A61K 31/222* (2013.01); *A61Q 11/00* (2013.01)

(58) Field of Classification Search
CPC ............ A61Q 11/00; A61K 8/37; A61K 8/34; A61K 8/347; A61K 9/0058; A61K 31/045; A61K 31/05; A61K 31/085; A61K 31/222
See application file for complete search history.

(56) References Cited

U.S. PATENT DOCUMENTS

| | | | | |
|---|---|---|---|---|
| 1,346,337 | A * | 7/1920 | Roark .................... | A61L 9/04 |
| | | | | 424/76.3 |
| 5,094,842 | A * | 3/1992 | Riley ..................... | A61K 8/19 |
| | | | | 424/52 |
| 8,216,553 | B2 * | 7/2012 | Hughes ................... | A61P 43/00 |
| | | | | 424/56 |
| 2004/0253278 | A1 * | 12/2004 | Maxwell ................. | A61Q 11/00 |
| | | | | 424/600 |
| 2006/0140884 | A1 * | 6/2006 | Worrell .................. | A61Q 11/00 |
| | | | | 424/58 |
| 2007/0110676 | A1 * | 5/2007 | Clymer ................... | A61K 31/192 |
| | | | | 424/45 |

FOREIGN PATENT DOCUMENTS

| | | | | |
|---|---|---|---|---|
| CN | | 103451017 | | 12/2013 |
| CN | | 104606100 | | 5/2015 |
| EP | | 1236461 A1 * | 9/2002 | ............. A61Q 11/00 |
| JP | | H07145598 | | 6/1995 |
| WO | WO-2014087419 A1 * | 6/2014 | ........... A61K 31/085 |
| WO | WO-2014087420 A1 * | 6/2014 | ........... A61K 31/085 |

OTHER PUBLICATIONS

M. Tiziana Baratta, H. J. Damien Dorman, S. G. Deans, A. C. Figueiredo, J. G. Barroso, and J. Ruberto. Antimicrobial and antioxidant properties. Flavour and Fragrance Journal, 13, 235-244 (1998) (Year: 1998).*
Google patent search_toothpaste thymol menthol Oct. 7, 2019 (Year: 2019).*
Google patent search_reducing burning flavor of menthol Feb. 1, 2020 (Year: 2020).*
Google Scholar Search_Jul. 10, 2020_essential oil composition carvacrol menthone (Year: 2020).*
Google Patent Search_Jul. 10, 2020_toothpaste with oregano oil (Year: 2020).*
S. Ekren, et al. "Chemical composition, antimicrobial activity and antioxidant capacity of some medicinal and aromatic plant extracts," African Journal of Microbiology Research vol. 7(5), pp. 383-388, Jan. 29, 2013. (Year: 2013).*
K. Chaieb, et al. "The Chemical Composition and Biological Activity of Clove Essential Oil, Eugenia caryophyllata (Syzigium aromaticum L. Myrtaceae): A Short Review," Phytother. Res. 21, 501-506 (2007). (Year: 2007).*
International Search Report and Written Opinion for PCT Application PCT/EP2016/060932 dated Aug. 31, 2016, pp. 1-12.

(Continued)

*Primary Examiner* — Michael P Cohen
(74) *Attorney, Agent, or Firm* — Timothy H. Van Dyke; WOLTER, VAN DYKE, DAVIS, PLLC

(57) ABSTRACT

The invention relates to aroma preparations that contain (a) a compound of the formula (I) in which R1 represents a linear or branched, saturated or unsaturated hydrocarbon group with 1 to 4 carbon atoms, R2 represents hydrogen or a hydroxyl group and R3 represents hydrogen, a methyl or methoxy group, or an essential oil containing one or more compounds of the formula (I) and at least one menthol compound.

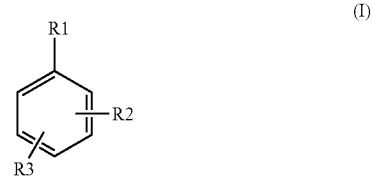

(I)

7 Claims, No Drawings

(56) References Cited

OTHER PUBLICATIONS

Mistine, "Peppermint Flavoured Herbal Extract Mouthwash", GNPD Mintel, pp. 1-2 (2014).
Xu, Jian-Guo et al., "Chemical Composition, Antibacterial Properties and Mechanism of Action of Essential Oil from Clove Buds against *Staphylococcus aureus*", Molecules, 2016, vol. 21, 1194, 13 pages.

* cited by examiner

MENTHOL-CONTAINING AROMA PREPARATIONS

CROSS-REFERENCE TO RELATED APPLICATION

This application is a national stage entry of and claims priority to PCT/EP2016/060932, filed May 14, 2016, which is hereby incorporated by reference in its entirety.

FIELD OF THE INVENTION

The invention lies in the field of aroma substances and relates to novel preparations comprising selected aroma and cooling substances as well as to oral preparations comprising these mixtures.

BACKGROUND OF THE INVENTION

4-Allyl-2-methoxyphenol, which is also referred to as eugenol, is a known fragrance and aroma substance with a warm-spicy note, which is a constituent of various essential oils such as clove oil (70 to 95% by weight), pimento and pimento leaf oil (60 to 90% by weight), bay oil (50 to 60% by weight) or the group of the cinnamon oils (5 to 95% by weight). In addition, it is found in laurel, basil, bananas, cherries and nutmeg. Eugenol, and especially clove oil, is frequently used in oral preparations, especially oral care products, because it has antiviral, antibacterial and antioxidative properties. For example, small amounts of eugenol improve the antibacterial properties of thymol and terpineol (EP 2480090 B1, UNILEVER).

However, it is a disadvantage that many people dislike the taste of eugenol, or clove oil, because they associate it with an unpleasant visit to the dentist. Eugenol is in fact also an integral constituent of so-called zinc oxide-eugenol cement, which is frequently used in dentistry. The same applies to structurally related substances, such as, for example, anethol, thymol or carvacrol.

A further disadvantage of these substances is that they can not only generate a desired warm-spicy taste impression but are also perceived by many consumers as being burning or even painful.

The object of the present was therefore to modify the taste impression of the mentioned substances, or essential oils containing them, so that the warm-spicy impression is enhanced and the burning-painful impression is suppressed.

DESCRIPTION OF THE INVENTION

A first subject of the invention therefore relates to aroma preparations comprising
(a) a compound of formula (I)

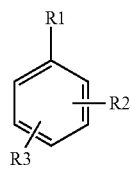

in which R1 represents a linear or branched, saturated or unsaturated hydrocarbon radical having from 1 to 4 carbon atoms, R2 represents hydrogen or a hydroxyl group and R3 represents hydrogen, a methyl or methoxy group, or an essential oil containing one or more compounds of formula (I), and
(b) at least one menthol compound.

Surprisingly, it has been found that the addition of menthol compounds, in particular of menthol, menthyl acetate and most particularly preferably of mixtures of menthol and menthyl acetate, fulfils the object formulated at the beginning in full. The mixtures continue to have a warm-spicy impression, but it is no longer burning or even painful and can only vaguely be associated with a visit to the dentist.

Compounds of Formula (I) and Essential Oils

Within the meaning of the present invention, preference is given to those compounds of formula (I) in which R1 represents a $-C(CH_3)_2$, $-CH_2-CH=CH_2$ or $-CH=CH-CH_3$ group. It is likewise structurally preferred that R2 and R3 do not both simultaneously represent hydrogen.

Concrete forms of the compounds of formula (I) are:

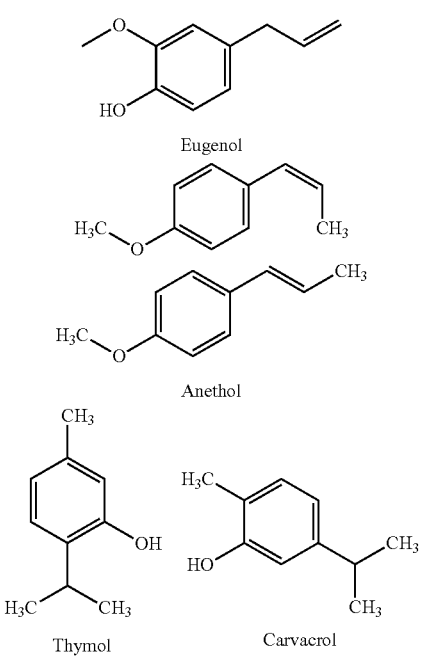

In addition to the basic structure eugenol there further come into consideration as component (a) also the essential oils already mentioned at the beginning, that is to say pimento oil, pimento leaf oil, bay oil, cinnamon oil, laurel oil, nutmeg oil and in particular clove oil.

Anethol is a constituent of anise oil, for example. Thymol and its isomer carvacrol are found as constituents of the essential oil of thyme, oregano and savory.

For clarification, it is noted that, instead of the individual compounds of formula (I), it is also possible to use mixtures, in particular mixtures of eugenol, anethol, thymol and/or carvacrol. The same applies to essential oils—such as, for example, those mentioned above—which one or more compounds of formula (I), especially eugenol, anethol, thymol and/or carvacrol, in virtually any desired relative proportions.

Menthol and Menthol Compounds

Menthol compounds which can be used within the meaning of the invention as component (b) are—in addition to the basic structure menthol itself—selected, for example, from the group formed by menthol methyl ether, menthone glyceryl acetal (FEMA GRAS[1] 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl N-ethyl oxamate, monomethyl succinate (FEMA GRAS 3810), monomenthyl glutarate (FEMA GRAS 4006), menthoxy-1,2-propanediol (FEMA GRAS 3784), menthoxy-2-methyl-1,2-propanediol (FEMA GRAS 3849) and also the menthanecarboxylic acid esters and amides WS-3, WS-4, WS-5, WS-12, WS-14 and WS-30 and mixtures thereof.

[1] FEMA stands for "Flavor and Extracts Manufacturers Association" and GRAS is defined as "Generally Regarded As Safe". A FEMA GRAS designation means that the substance so characterized is tested according to a standard method and is considered toxicologically harmless.

A first important representative of the substances that form component (b) is monomenthyl succinate (FEMA GRAS 3810), which was patented as a substance as early as 1963 by Brown & Williamson Tobacco Corp. (U.S. Pat. No. 3,111,127) and as a cooling agent is the subject of property rights U.S. Pat. Nos. 5,725,865 and 5,843,466 (V. Mane Fils). Both the succinate and the analogous monomenthyl glutarate (FEMA GRAS 4006) are important representatives of monomenthyl esters based on di- and poly-carboxylic acids:

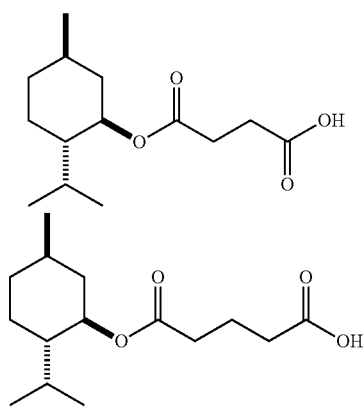

Examples of applications of these substances are to be found, for example, in publications WO 2003 043431 (Unilever) or EP 1332772 A1 (IFF).

The next important group of menthol compounds which are preferred within the meaning of the invention comprises carbonate esters of menthol and polyols, such as, for example, glycols, glycerol or carbohydrates, such as, for example, menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849) or the corresponding sugar derivatives:

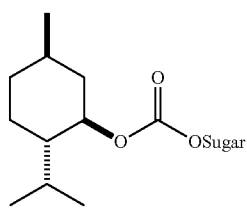

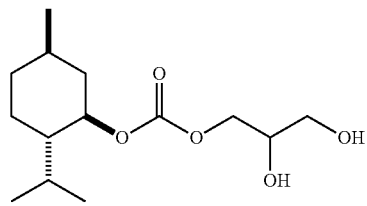

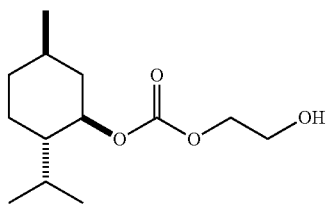

Menthol ethylene glycol carbonate

The use of such substances as a cooling substance for cigarettes is the subject, for example, of publication U.S. Pat. No. 3,419,543 (Mold et al.) from 1968; use as a physiological cooling agent is claimed in DE 4226043 A1 (H&R).

Preference is given within the meaning of the invention to the menthol compounds menthyl lactate (FEMA GRAS 3748=Frescolat® ML) and in particular menthone glyceryl acetal (FEMA GRAS 3807) or menthone glyceryl ketal (FEMA GRAS 3808), which is marketed under the name Frescolat® MGA.

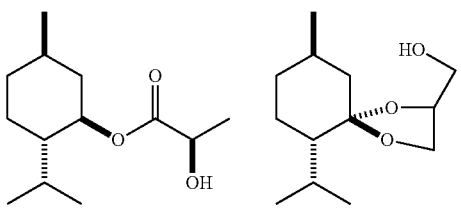

The former structure is obtained by esterification of lactic acid with menthol, the latter by acetalization of menthone with glycerol (see DE 2608226 A1, H&R). This group of compounds also includes 3-(1-menthoxy)-1,2-propanediol, which is also known as Cooling Agent 10 (FEMA GRAS 3784, see U.S. Pat. No. 6,328,982, TIC), and also 3-(1-menthoxy)-2-methyl-1,2-propanediol (FEMA GRAS 3849), which has an additional methyl group.

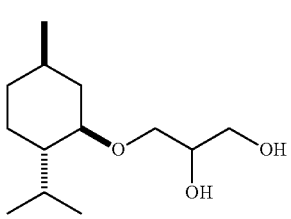

Cooling Agent 10

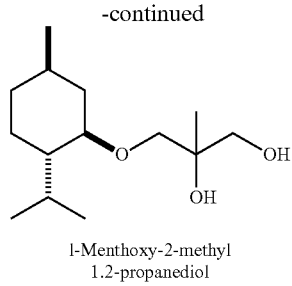

l-Menthoxy-2-methyl
1,2-propanediol

The preparation of 3-(1-menthoxy)-1,2-propanediol is carried out, for example, starting from menthol in accordance with the following scheme (see U.S. Pat. No. 4,459,425, Takagaso):

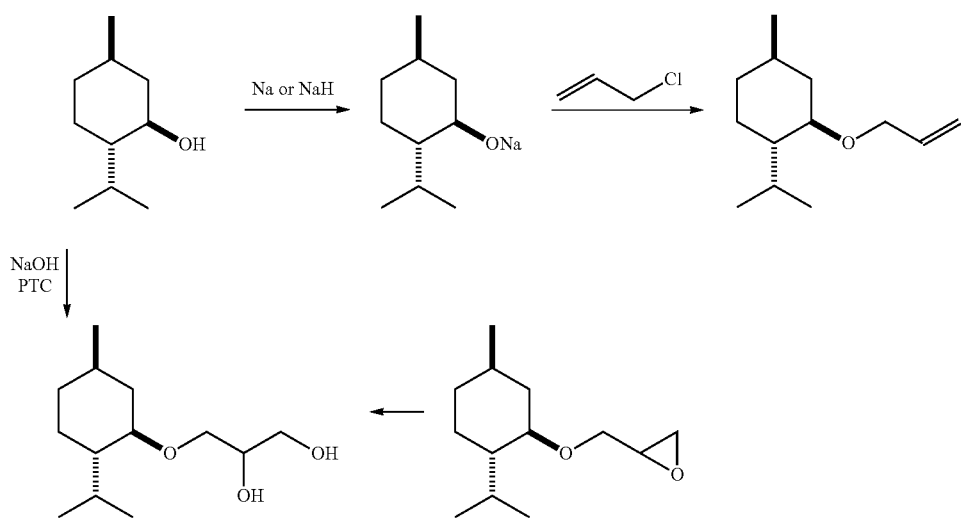

Alternative routes, in which menthol is reacted with epichlorohydrin in the first stage, are described in U.S. Pat. Nos. 6,407,293 and 6,515,188 (Takagaso). An overview of the preferred menthol compounds, which are distinguished by a CO bond, is given below:

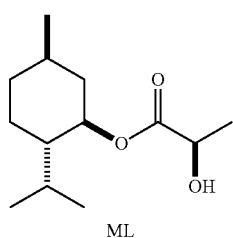

ML

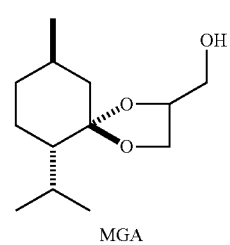

MGA

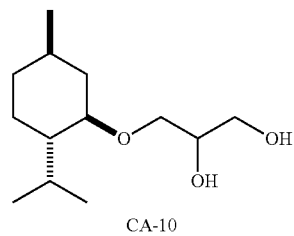

CA-10

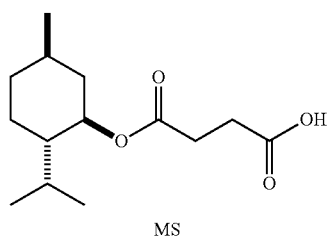

MS

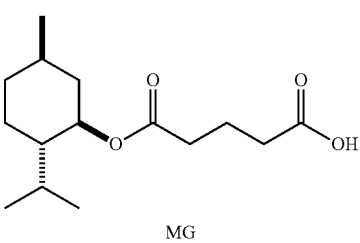

MG

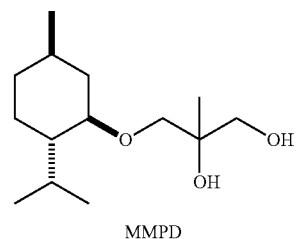

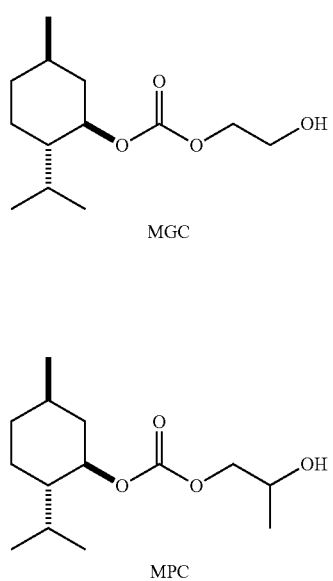

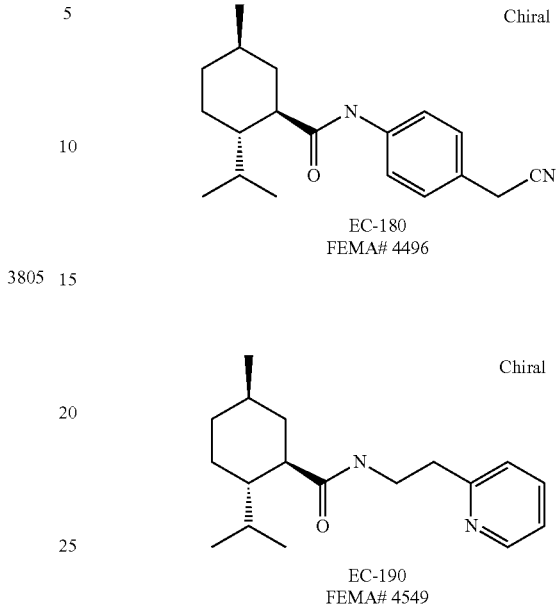

Of those substances, menthone glyceryl acetal/ketal and also menthyl lactate and also menthol ethylene glycol carbonate and menthol propylene glycol carbonate, which are marketed by the applicant under the names Frescolat® MGA, Frescolat® ML, Frescolat® MGC and Frescolat® MPC, have been found to be very particularly advantageous.

Likewise suitable are the two cooling substances EC-180 (FEMA GRAS 4496), EC-190 (FEMA GRAS 4549):

In the 70s of the last century, menthol compounds having a C—C bond in the 3-position were developed for the first time, and a number of representatives of these compounds can likewise be used within the meaning of the invention. These substances are referred to generally as WS types. The basic structure is a menthol derivative in which the hydroxyl group has been replaced by a carboxyl group (WS-1). All further WS types, such as, for example, the species WS-3, WS-4, WS-5, WS-12, WS-14 and WS-30 which are likewise preferred within the meaning of the invention, are derived from that structure. The following two diagrams show the synthesis routes:

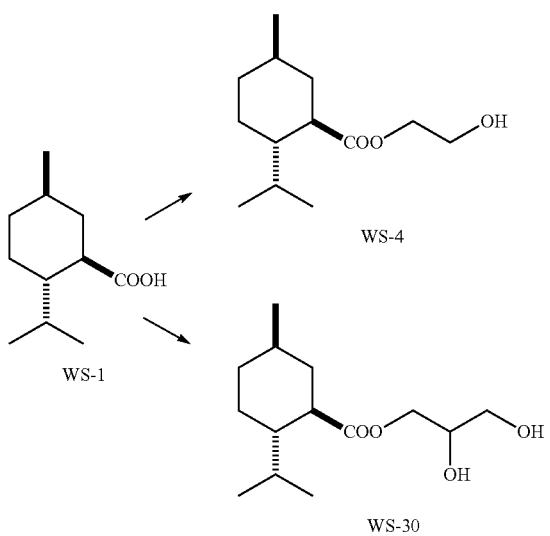

-continued

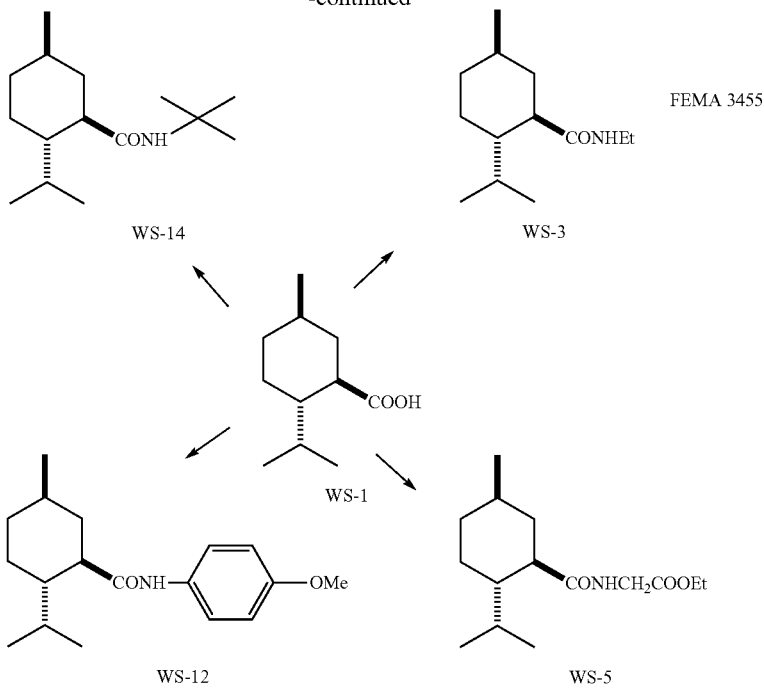

The esters derived from WS-1 are described, for example, in U.S. Pat. No. 4,157,384, while the corresponding N-substituted amides are described in J. Soc. Cosmet. Chem. p. 185-200 (1978).

Aroma Preparations

In a preferred embodiment, the preparations can comprise components (a) and (b) in a weight ratio of from approximately 80:20 to approximately 99:1 and preferably from approximately 85:15 to approximately 95:5. If a mixture of menthol and menthyl acetate is used as a component, the weight ratio of the two substances can advantageously be in the range of from 99:1 to 1:99, preferably approximately from 80:20 to 20:80 and in particular from approximately 60:40 to approximately 40:60.

Particular preference is given to aroma preparations which comprise
(a) from 80 to 99% by weight of compounds of formula (I) or of an essential oil containing one or more compounds of formula (I),
(b1) from 1 to 20% by weight menthol, and
(b2) from 1 to 20% by weight menthyl acetate,
with the proviso that the indicated amounts in each case add up to 100% by weight. This limitation makes it clear that any mixing ratios which do not add up to 100% by weight are excluded and the person skilled in the art can select any desired mixing ratios, within the specified limits, which fulfill the teaching outlined above without having to be inventively active for that purpose. Reference is additionally made to the implementation examples.

INDUSTRIAL APPLICABILITY

A further subject of the present invention relates to preparations for oral ingestion, comprising the above-described aroma mixtures. These preparations can be foodstuffs, pharmaceutical preparations or oral and tooth care agents, the transition between these groups being fluid. A chewing sweet can be used, for example, both as a sweet and as a cold relief agent, while a chewing gum can likewise be used for the purpose of freshening or for medicinal tooth care.

Oral Preparations

Typical examples of foodstuffs which comprise the preparations according to the invention are hard caramels, chewing sweets or chewing gums.

Typical examples of pharmaceutical preparations which comprise the preparations according to the invention are cold relief syrups, cold relief sprays or cold relief sweets.

Typical examples of pharmaceutical preparations which comprise the preparations according to the invention are toothpastes, mouthwashes or medicinal chewing gums.

The mentioned oral preparations can comprise the aroma mixtures in amounts of from approximately 0.5 to approximately 5% by weight and in particular from approximately 1 to approximately 2.5% by weight—based on the final preparation. In the following, auxiliary substances and additives which may likewise be contained in the oral preparations are described.

Foodstuffs

Foodstuffs which comprise the aroma mixtures according to the invention are generally hard caramels and chewing or boiled sweets. The most important additive for these products are sweeteners, including especially those which are not sugar-based. In addition, mention may also be made especially of further aromas and food colorings.

Sweeteners

Suitable sweeteners or sweet-tasting additives are firstly carbohydrates and especially sugars, such as, for example, sucrose/saccharose, trehalose, lactose, maltose, melicitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde or maltodextrin. Also suitable are plant preparations which contain those substances, for example based on sugar beets (*Beta vulgaris* ssp., sugar fractions, sugar syrup, molasses), sugar cane (*Saccharum officinarum* ssp., molasses, sugar cane syrup), maple syrup (*Acer* ssp.) or agave (agave syrup).

There come into consideration also synthetic, that is to say generally enzymatically produced, starches or sugar hydrolyzates (invert sugar, fructose syrup);

fruit concentrates (e.g. based on apples or pears);

sugar alcohols (e.g. erythritol, threitol, arabitol, ribotol, xylitol, sorbitol, mannitol, dulcitol, lactitol);

proteins (e.g. miraculin, monellin, thaumatin, curculin, brazzein);

sweeteners (e.g. magap, sodium cyclamate, acesulfame K, neohesperidine dihydrochalcone, saccharin sodium salt, aspartame, superaspartame, neotame, alitame, sucralose, stevioside, rebaudioside, lugduname, carrelame, sucrononate, sucrooctate, monatin, phenylodulcin);

sweet-tasting amino acids (e.g. glycine, D-leucine, D-threonine, D-asparagine, D-phenylalanine, D-tryptophan, L-proline);

further sweet-tasting low molecular weight substances, such as, for example, hernandulcin, dihydrochalcone glycosides, glycyrrhizin, glycyrrhetinic acid, derivatives and salts thereof, extracts of licorice (*Glycyrrhizza glabra* ssp.), *Lippia dulcis* extracts, *Momordica* ssp. extracts, or single substances such as, for example, *Momordica grosvenori* [Luo Han Guo] and the mogrosides obtained therefrom, *Hydrangea dulcis* or *Stevia* ssp. (e.g. *Stevia rebaudiana*) extracts.

Further Aroma Substances

The invention also permits the use in the oral preparations in particular of further aroma substances having an ester, aldehyde or lactone structure, which are broken down particularly quickly in the presence titanium dioxide and under the influence of light. The invention accordingly ensures improved stability, especially storage stability, of the aroma substances.

The oral preparations according to the invention can comprise one or more additional aroma substances. Typical examples include: acetophenone, allyl caproate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl caproate, butylidene-phthalide, carvone, camphene, caryophyllene, cineol, cinnamyl acetate, citral, citronellol, citronellal, citronellyl acetate, cyclohexyl acetate, cymene, damascone, decalactone, dihydrocoumarin, dimethyl anthranilate, dodecalactone, ethoxyethyl acetate, ethylbutyric acid, ethyl butyrate, ethyl caprinate, ethyl caproate, ethyl crotonate, ethyl furaneol, ethylguaiacol, ethyl isobutyrate, ethyl isovalerate, ethyl lactate, ethylmethyl butyrate, ethyl propionate, eucalyptol, eugenol, ethyl heptylate, 4-(p-hydroxyphenyl)-2-butanone, gamma-decalactone, geraniol, geranyl acetate, grapefruit aldehyde, methyl dihydrojasmonate (e.g. Hedion®), heliotropine, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl caproate, trans-2-hexenyl caproate, cis-3-hexenyl formate, cis-2-hexyl acetate, cis-3-hexyl acetate, trans-2-hexyl acetate, cis-3-hexyl formate, para-hydroxybenzyl-acetone, isoamyl alcohol, isoamyl isovalerate, isobutyl butyrate, isobutyraldehyde, isoeugenol methyl ether, isopropylmethylthiazole, lauric acid, levulinic acid, linalool, linalool oxide, linalyl acetate, menthol, menthofuran, methyl anthranilate, methylbutanol, methylbutyric acid, 2-methylbutyl acetate, methyl caproate, methyl cinnamate, 5-methylfural, 3,2,2-methylcyclopentenolone, 6,5,2-methylheptenone, methyl dihydrojasmonate, methyl jasmonate, 2-methylmethyl butyrate, 2-methyl-2-pentenoic acid, methyl thiobutyrate, 3,1-methylthiohexanol, 3-methylthiohexyl acetate, nerol, neryl acetate, trans,trans-2,4-nonadienal, 2,4-nonadienol, 2,6-nonadienol, nootkatone, delta-octalactone, gamma-octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl isovalerate, piperonal, propionaldehyde, propyl butyrate, pulegone, pulegol, sinensal, sulfurol, terpinene, terpineol, terpinolene, 8,3-thiomenthanone, 4,4,2-thiomethylpentanone, thymol, delta-undecalactone, gamma-undecalactone, valencene, valeric acid, vanillin, acetoin, ethylvanillin, ethylvanillin isobutyrate (=3-ethoxy-4-isobutyryloxybenzaldehyde), 2,5-dimethyl-4-hydroxy-3(2H)-furanone and its derivatives (preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (preferably ethylmaltol), coumarin and coumarin derivatives, gamma-lactones (preferably gamma-undecalactone, gamma-nonalactone, gamma-decalactone), delta-lactones (preferably 4-methyldeltalactone, massoilactone, delta-decalactone, tuberolactone), methyl sorbate, divanillin, 4-hydroxy-2(or 5)-ethyl-5(or 2)-methyl-3(2H)-furanone, 2-hydroxy-3-methyl-2-cyclopentenone, 3-hydroxy-4,5-dimethyl-2(5H)-furanone, acetic acid isoamyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid n-butyl ester, n-octanoic acid ethyl ester, ethyl-3-methyl-3-phenyl glycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furan, 2-methyl-3-furanthiol, bis(2-methyl-3-furyl) disulfide, furfurylmercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethyl-pyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxy-pyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnam-aldehyde, cinnamic alcohol, methyl salicylate, isopulegol, and stereoisomers, enantiomers, position isomers, diastereoisomers, cis/trans isomers and epimers (not mentioned explicitly here) of those substances.

Taste Enhancers

The oral preparations can also comprise substances for enhancing a salty, optionally slightly acidic and/or umami taste impression. The products, or aroma mixtures, according to the invention are accordingly used in combination with at least one further substance suitable for enhancing a pleasant taste impression (salty, umami, optionally slightly acidic). Preference is given here to compounds having a salty taste and salt-enhancing compounds. Preferred compounds are disclosed in WO 2007/045566. Also preferred are umami compounds as described in WO 2008/046895 and EP 1 989 944.

Products which are preferred according to the invention can further also comprise aroma substances for masking bitter and/or astringent taste impressions (taste-correcting agents). The (further) taste-correcting agents are selected, for example, from the following list: nucleotides (e.g. adenosine 5'-monophosphate, cytidine 5'-monophosphate) or pharmaceutically acceptable salts thereof, lactisole, sodium salts (e.g. sodium chloride, sodium lactate, sodium citrate, sodium acetate, sodium gluconate), further hydroxyflavanones (e.g. eriodictyol, homoeriodictyol or sodium salts thereof), in particular according to US 2002/0188019, hydroxybenzoic acid amides according to DE 10 2004 041 496 (e.g. 2,4-dihydroxybenzoic acid vanillylamide, 2,4-dihydroxybenzoic acid N-(4-hydroxy-3-methoxybenzyl)-amide, 2,4,6-trihydroxybenzoic acid N-(4-hydroxy-3-methoxybenzyl)amide, 2-hydroxybenzoic acid N-4-(hydroxy-3-methoxybenzyl)amide, 4-hydroxybenzoic acid N-(4-hydroxy-3-methoxybenzyl)amide, 2,4-dihydroxy-benzoic acid N-(4-hydroxy-3-methoxybenzyl)amide monosodium salt, 2,4-dihydroxybenzoic acid N-2-(4-hydroxy-3-methoxyphenyl)ethylamide, 2,4-dihydroxy-benzoic acid N-(4-hydroxy-3-ethoxybenzyl)amide, 2,4-dihydroxybenzoic acid N-(3,4-dihydroxybenzyl)amide and 2-hydroxy-5-methoxy-N-[2-(4-hydroxy-3-methoxyphenyl)-ethyl]amide (aduncamide), 4-hydroxybenzoic acid vanillylamide), bitter-masking hydroxydeoxybezoins, for example according to WO 2006/106023 (e.g. 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)-ethanone, 1-(2-hydroxy-4-methoxyphenyl)-2-(4-hydroxy-3-methoxyphenyl) ethanone, amino acids (e.g. gamma-aminobutyric acid according to WO 2005/096841 for reducing or masking an unpleasant taste impression such as bitterness), malic acid glycosides according to WO 2006/003107, mixtures having a salty taste according to PCT/EP 2006/067120, diacetyl trimers according to WO 2006/058893, mixtures of whey proteins with lecithins and/or bitter-masking substances such as gingerdiones according to WO 2007/003527.

Preferred aroma substances are those which cause a sweet odor impression, wherein the further aroma substance or substances which cause a sweet odor impression are preferably selected from the group consisting of:

vanillin, ethyl vanillin, ethyl vanillin isobutyrate (=3-ethoxy-4-isobutyryloxybenzaldehyde), furaneol (2,5-dimethyl-4-hydroxy-3(2H)-furanone) and derivatives (e.g. homofuraneol, 2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone), maltol and derivatives (e.g. ethyl maltol), coumarin and derivatives, gamma-lactones (e.g. gamma-undecalactone, gamma-nonalactone), delta-lactones (e.g. 4-methyldeltalactone, massoilactone, delta-decalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, fruit esters and fruit lactones (e.g. acetic acid n-butyl ester, acetic acid isoamyl ester, propionic acid ethyl ester, butyric acid ethyl ester, butyric acid n-butyl ester, butyric acid isoamyl ester, 3-methylbutyric acid ethyl ester, n-hexanoic acid ethyl ester, n-hexanoic acid allyl ester, n-hexanoic acid n-butyl ester, n-octanoic acid ethyl ester, ethyl 3-methyl-3-phenylglycidate, ethyl 2-trans-4-cis-decadienoate), 4-(p-hydroxyphenyl)-2-butanone, 1,1-dimethoxy-2,2,5-trimethyl-4-hexane, 2,6-dimethyl-5-hepten-1-al, 4-hydroxycinnamic acid, 4-methoxy-3-hydroxycinnamic acid, 3-methoxy-4-hydroxycinnamic acid, 2-hydroxycinnamic acid, 2,4-dihydroxybenzoic acid, 3-hydroxybenzoic acid, 3,4-dihydroxybenzoic acid, vanillic acid, homovanillic acid, vanillomandelic acid and phenylacetaldehyde.

Active Ingredients for Masking Unpleasant Taste Impressions

The oral preparations can further also comprise substances which likewise serve to mask bitter and/or astringent taste impressions. These further taste-correcting agents are selected, for example, from the following list: nucleotides (e.g. adenosine 5'-monophosphate, cytidine 5'-monophosphate) or physiologically acceptable salts thereof, lactisole, sodium salts (e.g. sodium chloride, sodium lactate, sodium citrate, sodium acetate, sodium gluconate), hydroxyflavanones, preferably eriodictyol, sterubin (eriodictyol 7-methyl ether), homoeriodictyol and the sodium, potassium, calcium, magnesium or zinc salts thereof (in particular those as described in EP 1258200 A2, which in respect of the corresponding compounds disclosed therein is incorporated by reference in this application), hydroxybenzoic acid amides, preferably 2,4-dihydroxybenzoic acid vanillylamide, 2,4-dihydroxy-benzoic acid N-(4-hydroxy-3-methoxybenzyl)amide, 2,4,6-trihydroxybenzoic acid N-(4-hydroxy-3-methoxybenzyl)-amide, 2-hydroxybenzoic acid N-4-(hydroxy-3-methoxy-benzyl)amide, 4-hydroxybenzoic acid N-(4-hydroxy-3-methoxybenzyl)amide, 2,4-dihydroxybenzoic acid N-(4-hydroxy-3-methoxybenzyl)amide monosodium salt, 2,4-dihydroxybenzoic acid N-(2-(4-hydroxy-3-methoxyphenyl)-ethylamide, 2,4-dihydroxybenzoic acid N-(4-hydroxy-3-ethoxybenzyl)amide, 2,4-dihydroxybenzoic acid N-(3,4-dihydroxybenzyl)amide and 2-hydroxy-5-methoxy-N-[2-(4-hydroxy-3-methoxyphenyl)ethyl]amide; 4-hydroxybenzoic acid vanillylamides (in particular those as described in WO 2006/024587, which in respect of the corresponding compounds disclosed therein is incorporated by reference in this application); hydroxydeoxybenzoins, preferably 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)-ethanone and 1-(2-hydroxy-4-methoxyphenyl)-2-(4-hydroxy-3-methoxyphenyl)ethanone) (in particular those as described in WO 2006/106023, which in respect of the corresponding compounds disclosed therein is incorporated by reference in this application); hydroxyphenylalkanediones, such as, for example, [2]-gingerdione, [3]-gingerdione, [4]-gingerdione, [2]-dehydrogingerdione, [3]-dehydrogingerdione, [4]-dehydrogingerdione) (in particular those as described in WO 2007/003527, which in respect of the corresponding compounds disclosed therein is incorporated by reference in this application); diacetyl trimers (in particular those as described in WO 2006/058893, which in respect of the corresponding compounds disclosed therein is incorporated by reference in this application); gamma-aminobutyric acids (in particular those as described in WO 2005/096841, which in respect of the corresponding compounds disclosed therein is incorporated by reference in this application); divanillins (in particular those as described in WO 2004/078302, which in respect of the corresponding compounds disclosed therein is incorporated by reference in this application) and 4-hydroxydihydrochalcones (preferably as described in US 2008/0227867 A1, which in respect of the corresponding compounds disclosed therein is incorporated by reference in this application), in particular phloretin and davidigenin, amino acids or mixtures of whey proteins with lecithins, hesperetin as disclosed in WO 2007/014879, which in respect of those compounds is incorporated by reference in this application, 4-hydroxydihydrochalcones as disclosed in WO 2007/107596, which in respect of those compounds is incorporated by reference in this application, or propenylphenyl glycosides (chavicol glycosides) as described in EP 1955601 A1, which in respect of those compounds is incorporated by reference in this application, or extracts of *Rubus suavissimus*, extracts of *Hydrangea macrophylla* as described in EP 2298084 A1, pellitorine and derived aroma compositions as described in EP 2008530 A1, umami compounds as described in WO 2008/046895 A1 and EP 1989944 A1, umami compounds as described in EP 2064959 A1 or EP 2135516 A1, vanillyl lignans, enterodiol, and also N-decadienoylamino acids and mixtures thereof.

Food Colorings

Food colorings, or colorings for short, are foodstuff additives for coloring foodstuffs. Colorings are divided into the groups natural colorings and synthetic colorings. Nature-identical colorings are likewise of synthetic origin. The nature-identical colorings are synthetic imitations of coloring substances which occur naturally. Suitable colorings for use in the present composition are selected from: curcumin, E 100 riboflavin, lactoflavin, laktoflavin, vitamin B2, E 101 tartrazine, E 102 Quinoline Yellow, E 104 Orange Yellow S, Orange Yellow RGL, E 110 cochineal, carminic acid, true carmine, E 120 azorubine, carmoisine, E 122 amaranth, E 123 Cochineal Red A, Ponceau 4 R, Brilliant Scarlet 4 R, E 124 erythrosine, E 127 Allura Red AC, E 129 Patent Blue V, E 131 indigotine, indigo carmine, E 132 Brilliant Blue FCF, Patent Blue AE, Amido Blue AE, E 133 chlorophylls, chlorophyllins, E 140 copper complexes of chlorophylls, copper-chlorophyllin complexes, E 141 Acid Brilliant Green, Green S, E 142 caramel color, E 150 a caustic sulfite caramel, E 150 b ammonia caramel, E 150 c sulfite ammonia caramel, E 150 d Brilliant Black FCF, Brilliant Black PN, Black PN, E 151 vegetable carbon, E 153 Brown FK, E 154 Brown HT, E 155 carotene, E 160 a annatto, bixin, norbixin, E 160 b capsanthin, capsorubin, E 160 c lycopene, E 160 d beta-apo-8'-carotenal, apocarotenal, beta-apocarotenal, E 160 e beta-apo-8'-carotenic acid ethyl ester (C30), apocarotene ester, beta-carotenic acid ester, E 160 f lutein, xanthophyll, E 161 b canthaxanthin, E 161 g betanin, beet red, E 162 anthocyanins, E 163 calcium carbonate, E 170 titanium dioxide, E 171 iron oxides, iron hydroxides, E 172 aluminum, E 173 silver, E 174 gold, E 175 Lithol Rubine BK, Pigment Rubine BK, E 180.

Chewing Gums

The preferred oral preparations can in particular also be chewing gums. Such products typically comprise a water-insoluble component and a water-soluble component.

The water-insoluble base, which is also referred to as the "gum base", conventionally comprises natural or synthetic elastomers, resins, fats and oils, plasticizers, fillers, colorings and optionally waxes. The proportion of base in the total composition is usually from 5 to 95, preferably from 10 to 50 and in particular from 20 to 35% by weight. In a typical embodiment of the invention, the base is composed of from 20 to 60% by weight synthetic elastomers, from 0 to 30% by weight natural elastomers, from 5 to 55% by weight plasticizers, from 4 to 35% by weight fillers and, in subordinate amounts, additives such as colorings, antioxidants and the like, with the proviso that they are water-soluble at most in small amounts.

Suitable synthetic elastomers are, for example, polyisobutylenes having average molecular weights (according to GPC) of from 10,000 to 100,000 and preferably from 50,000 to 80,000, isobutylene-isoprene copolymers ("butyl elastomers"), styrene-butadiene copolymers (styrene:butadiene ratio e.g. 1:3 to 3:1), polyvinyl acetates having average molecular weights (according to GPC) of from 2000 to 90,000 and preferably from 10,000 to 65,000, polyisoprenes, polyethylene, vinyl acetate-vinyl laurate copolymers and mixtures thereof. Examples of suitable natural elastomers are rubbers such as, for example, smoked or liquid latex or guayule as well as natural rubber substances such as jelutong, lechi-caspi, perillo, sorva, massaranduba balata, massaranduba chocolate, nispero, rosindinba, chicle, gutta hang lkang and mixtures thereof. The choice of the synthetic and natural elastomers and the mixing ratios thereof is governed substantially by whether bubbles are to be produced with the chewing gums ("bubble gums") or not. Elastomer mixtures comprising jelutong, chicle, sorva and massaranduba are preferably used.

In most cases, the elastomers are found to be too hard or to have too little deformability during processing, so that it has been found to be advantageous to use concomitantly special plasticizers, which must naturally in particular also satisfy all the requirements for approval as food additives. In this respect, there come into consideration especially esters of resin acids, for example esters of lower aliphatic alcohols or polyols with wholly or partially hardened, monomeric or oligomeric resin acids. In particular, the methyl, glycerol or pentaerythritol esters and mixtures thereof are used for this purpose. Alternatively, there also come into consideration terpene resins, which can be derived from alpha-pinene, beta-pinene, delta-limonene or mixtures thereof.

Suitable fillers or texturizers are magnesium or calcium carbonate, ground pumice, silicates, especially magnesium or aluminum silicates, clays, aluminum oxides. Talcum, titanium dioxide, mono-, di- and tri-calcium phosphate and cellulose polymers.

Suitable emulsifiers are tallow, hardened tallow, hardened or partially hardened vegetable oils, cocoa butter, partial glycerides, lecithin, triacetin and saturated or unsaturated fatty acids having from 6 to and preferably from 12 to 18 carbon atoms and mixtures thereof.

Suitable colorings and whitening agents are, for example, the FD and C types allowed for the coloring of foodstuffs, plant and fruit extracts and titanium dioxide.

The base masses can comprise waxes or be wax-free; examples of wax-free compositions are to be found inter alia in patent specification U.S. Pat. No. 5,286,500, the content of which is expressly incorporated herein by reference.

In addition to the water-insoluble gum base, chewing gum preparations generally comprise a water-soluble component formed, for example, by softeners, sweeteners, fillers, taste-imparting substances, taste enhancers, emulsifiers, colorings, acidifying agents, antioxidants and the like, here with the proviso that the constituents possess at least adequate water solubility. Depending on the water solubility of the specific representatives, individual constituents can accordingly belong both to the water-insoluble phase and to the water-soluble phase. However, it is also possible to use combinations, for example, of a water-soluble and a water-insoluble emulsifier, whereby the individual representatives are then in different phases. The water-insoluble component generally accounts for from 5 to 95 and preferably from 20 to 80% by weight of the preparation.

Water-soluble softeners or plasticizers are added to the chewing gum compositions in order to improve the chewability and the chewing sensation and are present in the mixtures typically in amounts of from 0.5 to 15% by weight. Typical examples are glycerol, lecithin and aqueous solutions of sorbitol, hardened starch hydrolyzates or corn syrup.

Suitable sweeteners are both sugar-containing and sugar-free compounds, which are used in amounts of from 5 to 95, preferably from 20 to 80 and in particular from 30 to 60% by weight, based on the chewing gum composition. Typical saccharide sweeteners are sucrose, dextrose, maltose, dextrin, dried invert sugar, fructose, levulose, galactose, corn syrup and mixtures thereof. Suitable sugar substitutes are sorbitol, mannitol, xylitol, hardened starch hydrolyzates, maltitol and mixtures thereof. There further come into consideration as additives also so-called HIAS (high intensity artificial sweeteners), such as, for example, sucralose, aspartame, acesulfame salts, alitame, saccharin and saccharin salts, cyclamic acid and salts thereof, glycyrrhizins, dihydrochalcones, thaumatin, monellin and the like, on their own or in blends. Particularly effective are also the hydrophobic HIAS which are the subject of international patent application WO 2002 091849 A1 (Wrigleys) and also *stevia* extracts and the active constituents thereof, in particular rebeaudioside A. The amount of these substances that is used depends especially on their power and is typically in the range of from 0.02 to 8% by weight.

Fillers such as, for example, polydextrose, raftilose, raftiline, fructooligosaccharides (NutraFlora), palatinose oligosaccharides, guar gum hydrolyzates (Sun Fiber) and dextrins are suitable in particular for the production of low-calorie chewing gums.

The choice of further taste-imparting substances is virtually unlimited and is not critical for the nature of the invention. The total content of all taste-imparting substances is usually from 0.1 to 15 and preferably from 0.2 to 5% by weight, based on the chewing gum composition. Suitable further taste-imparting substances are, for example, essential oils, synthetic aromas and the like, such as, for example, anise oil, star anise oil, caraway oil, *eucalyptus* oil, fennel oil, lemon oil, wintergreen oil, clove oil and the like, as are also used, for example, in oral and tooth care agents.

The chewing gums can further comprise auxiliary substances and additives which are suitable, for example, for tooth care, especially for controlling plaque and gingivitis, such as, for example, chlorhexidine, CPC or triclosan. pH regulators (e.g. buffers or urea), active ingredients against caries (e.g. phosphates or fluorides), biogenic active ingredients (antibodies, enzymes, caffeine, plant extracts) can further be present, provided these substances are approved for foodstuffs and do not interact with one another in an undesirable manner.

Oral and Tooth Care Agents

Orally consumable sweet-tasting products according to the invention can in particular serve for oral and tooth cleaning and care. Examples thereof are, as mentioned, toothpastes, tooth gels, tooth powders, mouthwashes and the like. Toothpastes or tooth creams are generally understood as being preparations in gel or paste form comprising water, thickeners, humectants, abrasive or cleaning particles, surfactants, sweeteners, aroma substances, deodorizing active ingredients and also active ingredients against oral and tooth diseases. All conventional cleaning particles, such as, for example, chalk, dicalcium phosphate, insoluble sodium metaphosphate, aluminum silicates, calcium pyrophosphate, finely divided synthetic resins, silicas, aluminum oxide and aluminum oxide trihydrate, can be used in the toothpastes according to the invention.

Cleaning particles which are preferably suitable for the toothpastes according to the invention are especially finely divided xerogel silicas, hydrogel silicas, precipitated silicas, aluminum oxide trihydrate and finely divided alpha-aluminum oxide or mixtures of these cleaning particles in amounts of from 15 to 40% by weight of the toothpaste. Suitable as humectants are predominantly low molecular weight polyethylene glycols, glycerol, sorbitol or mixtures of these products in amounts of up to 50% by weight. Among the known thickeners there are suitable the thickening, finely divided gel silicas and hydrocolloids, such as, for example, carboxymethylcellulose, hydroxyethyl-cellulose, hydroxypropyl guar, hydroxyethyl starch, polyvinylpyrrolidone, high molecular weight polyethylene glycol, plant gums such as tragacanth, agar-agar, carrageen moss, gum arabic, xanthan gum and carboxyvinyl polymers (e.g. Carbopol® types). In addition to the mixtures of menthofuran and menthol compounds, the oral and tooth care agents can in particular comprise surface-active substances, preferably anionic and non-ionic high-foaming surfactants, such as the substances already mentioned above, but in particular alkyl ether sulfate salts, alkyl polyglucosides and mixtures thereof.

Further conventional toothpaste additives are:

preservatives and antimicrobial substances such as, for example, p-hydroxybenzoic acid methyl, ethyl or propyl esters, sodium sorbate, sodium benzoate, bromochlorophene, phenylsalicylic acid ester, thymol and the like;

anti-calculus active ingredients, for example organophosphates such as 1-hydroxyethane-1,1-diphosphonic acid, 1-phosphonpropane-1,2,3-tri-carboxylic acid and others, which are known, for example, from U.S. Pat. No. 3,488,419, DE 2224430 A1 and DE 2343196 A1;

other caries-inhibiting substances such as, for example, sodium fluoride, sodium monofluoro-phosphate, tin fluoride;

sweetening agents, such as, for example, sodium saccharin, sodium cyclamate, sucrose, lactose, maltose, fructose or Aspartame® (L-aspartyl-L-phenylalanine methyl ester), *stevia* extracts or sweetening constituents thereof, in particular rebeaudiosides;

additional aromas such as, for example, *eucalyptus* oil, anise oil, fennel oil, caraway oil, methyl acetate, cinnamaldehyde, anethol, vanillin, thymol and mixtures of these and other natural and synthetic aromas;

pigments such as, for example, titanium dioxide;

colorings;

buffer substances such as, for example, primary, secondary or tertiary alkali phosphates or citric acid/sodium citrate;

wound-healing and anti-inflammatory substances such as, for example, allantoin, urea, azulene, camomile active ingredients and acetylsalicylic acid derivatives.

A preferred form of the oral preparations is toothpastes in the form of an aqueous, pasty dispersion comprising polishing agents, humectants, viscosity regulators and optionally further conventional components, as well as the mixture of menthofuran and menthol compounds in amounts of from 0.5 to 2% by weight.

In mouthwashes, a combination with aqueous-alcoholic solutions containing different concentrations of essential oils, emulsifiers, astringent and tonifying drug extracts, calculus-inhibiting, antibacterial additives and taste-correcting agents is readily possible. A further preferred form of the invention is a mouthwash in the form of an aqueous or aqueous-alcoholic solution comprising the mixture of menthofuran and menthol compounds in amounts of from 0.5 to 2% by weight. In mouthwashes which are diluted prior to use, adequate effects can be achieved with higher concentrations, corresponding to the provided dilution ratio.

For improving the flow behavior, hydrotropes, such as, for example, ethanol, isopropyl alcohol, or polyols can further be used; these substances largely correspond to the carriers described at the beginning. Polyols which come into consideration here have preferably from 2 to 15 carbon atoms and at least two hydroxyl groups. The polyols can contain further functional groups, in particular amino groups, or can be modified with nitrogen. Typical examples are glycerol;

alkylene glycols, such as, for example, ethylene glycol, diethylene glycol, propylene glycol, butylene glycol, hexylene glycol and also polyethylene glycols having an average molecular weight of from 100 to 1000 daltons;

technical oligoglycerol mixtures having a degree of self-condensation of from 1.5 to 10, such as, for example, technical diglycerol mixtures having a diglycerol content of from 40 to 50% by weight;

methylol compounds, such as in particular tri-methylolethane, trimethylolpropane, trimethylol-butane, pentaerythritol and dipentaerythritol;

lower alkyl glucosides, in particular those having from 1 to 8 carbon atoms in the alkyl moiety, such as, for example, methyl and butyl glucoside;

sugar alcohols having from 5 to 12 carbon atoms, such as, for example, sorbitol or mannitol;

sugars having from 5 to 12 carbon atoms, such as, for example, glucose or saccharose;

amino sugars, such as, for example, glucamine;

dialcohol amines, such as diethanolamine or 2-amino-1,3-propanediol.

There are suitable as preservatives, for example, phenoxyethanol, formaldehyde solution, parabens, pentanediol or sorbic acid and also the silver complexes known by the name Surfacine® and the further substance classes listed in Annex 6, Part A and B of the cosmetics directive.

There may be mentioned as perfume oils mixtures of natural and synthetic fragrances. Natural fragrances are extracts of blossoms (lily, lavender, rose, jasmine, neroli, ylang-ylang), stems and leaves (geranium, patchouli, petitgrain), fruits (anise, coriander, caraway, juniper), fruit skins (bergamot, lemon, orange), roots (mace, *angelica*, celery, cardamon, costus, iris, calamus), woods (pine wood, sandalwood, guaiacum wood, cedar wood, rosewood), herbs and grasses (tarragon, lemongrass, sage, thyme), needles and branches (spruce, fir, pine, dwarf pine), resins and balsams (*galbanum*, elemi, benzoin, myrrh, olibanum, opoponax). Animal raw materials are also suitable, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert.-butyl cyclohexyl acetate, linalyl acetate, dimethylbenzylcarbinyl acetate, phenylethyl acetate, linalyl benzoate, benzyl formate, ethyl methylphenyl glycinate, allyl cyclohexyl propionate, styrallyl propionate and benzyl salicylate. The ethers include, for example, benzyl ethyl ether, the aldehydes include, for example, the linear alkanals having from 8 to 18 carbon atoms, citral, citronellal, citronellyl oxyacetaldehyde, cyclamen aldehyde, hydroxycitronellal, lilial and bourgeonal, the ketones include, for example, the ionones, α-isomethylionone and methyl cedryl ketone, the alcohols include anethol, citronellol, eugenol, isoeugenol, geraniol, linalool, phenylethyl alcohol and terpineol, the hydrocarbons include mainly the terpenes and balsams. Preference is given, however, to the use of mixtures of different fragrances which together produce an appealing fragrance note. Essential oils of relatively low volatility, which are used mostly as aroma components, are also suitable as perfume oils, for example sage oil, camomile oil, clove oil, melissa oil, mint oil, cinnamon leaf oil, lime blossom oil, juniper berry oil, vetiver oil, olibanum oil, *galbanum* oil, labdanum oil and lavandin oil. Preference is given to the use of bergamot oil, dihydromyrcenol, lilial, lyral, citronellol, phenylethyl alcohol, α-hexyl cinnamaldehyde, geraniol, benzylacetone, cyclamen aldehyde, linalool, Boisambrene Forte, Ambroxan, indole, hedione, sandelice, lemon oil, mandarin oil, orange oil, allylamyl glycolate, cyclovertal, lavandin oil, clary sage oil, β-damascone, geranium oil bourbon, cyclohexyl salicylate, Vertofix Coeur, Iso-E-Super, Fixolide NP, evernyl, iraldeine gamma, phenylacetic acid, geranyl acetate, benzyl acetate, rose oxide, romilat, irotyl and floramat, on their own or in mixtures.

There are suitable as aromas, for example, peppermint oil, spearmint oil, anise oil, star anise oil, caraway oil, *eucalyptus* oil, fennel oil, lemon oil, wintergreen oil, clove oil, menthol and the like.

Method and Use

A further subject of the invention relates to a method of enhancing the warm-spicy and reducing the burning, painful taste of compounds of formula (I) or an essential oil containing one or more compounds of formula (I), which method is distinguished in that there is added to preparations containing those substances at least one menthol compound, preferably in amounts of from approximately 0.5 to approximately 5% by weight.

A final subject of the invention relates to the use of menthol compounds for correcting the taste of compounds of formula (I) or essential oils containing one or more compounds of formula (I).

As far as the method and use as mentioned above are concerned, the same amounts and preferred forms as described in detail hereinbefore apply, without the need for any repetition.

EXAMPLES

Application Tests

Examples 1 to 4, Comparative Examples C1 to C2

The taste profile of various aroma mixtures was assessed by a panel consisting of 5 trained testers. To that end, the mixtures were incorporated in an amount of 0.5% by weight into an unsweetened and unflavored standard chewing sweet preparation. The results are reproduced in Table 1. The evaluation was made according to the rating (5)=is very true to (0)=is largely untrue. The mean values are given. Examples 1 to 4 are in accordance with the invention, while Examples C1 to C2 are for comparison purposes.

TABLE 1

| Sensory evaluation of aroma mixtures | | | | | | |
|---|---|---|---|---|---|---|
| Components | C1 | C2 | 1 | 2 | 3 | 4 |
| Eugenol | 100 | — | 80 | 80 | 80 | — |
| Clove oil | — | 100 | — | — | — | 80 |
| Menthol | — | — | 20 | — | 10 | 10 |
| Menthyl acetate | — | — | — | 20 | 10 | 10 |
| Sensory evaluation | | | | | | |
| Warm-spicy taste | 4.2 | 4.1 | 4.5 | 4.3 | 4.5 | 4.8 |
| Burning taste | 4.5 | 4.5 | 3.1 | 2.8 | 2.1 | 2.0 |
| Painful sensation | 3.0 | 2.9 | 1.5 | 1.5 | 1.0 | 1.0 |

The examples and comparative examples show that the mixtures according to the invention are evaluated in sensory terms significantly better than the individual substances.

A number of formulation examples are given hereinbelow.

FORMULATION EXAMPLES

Example 1

Toothpaste (amounts as % by weight)

| COMPONENTS | AMOUNT |
| --- | --- |
| Water (deionized) | to 100 |
| Sorbitol 70% | 45.00 |
| Trisodium phosphate | 0.10 |
| Saccharin | 0.20 |
| Sodium monofluorophosphate | 1.14 |
| PEG 1500 | 5.00 |
| Sident 9 (abrasive silica) | 10.00 |
| Sident 22 S (thickening silica) | 8.00 |
| Sodium carboxymethylcellulose | 1.10 |
| Titanium(IV) oxide | 0.50 |
| Water (deionized) | 4.50 |
| Sodium lauryl sulfate (SLS) | 1.50 |
| Aroma mixture | 1.00 |
| Solbrol M (sodium salt) (methylparaben) | 0.15 |
| Aroma mixture 3 | 0.40 |

Example 2

Toothpaste with zinc citrate (amounts as % by weight)

| COMPONENTS | AMOUNT |
| --- | --- |
| Water (deionized) | to 100 |
| Sorbitol 70% | 45.00 |
| Trisodium phosphate | 0.10 |
| Saccharin | 0.20 |
| Sodium monofluorophosphate | 1.14 |
| PEG 1500 | 5.00 |
| Sident 9 (abrasive silica) | 10.00 |
| Sident 22 S (thickening silica) | 8.00 |
| Sodium carboxymethylcellulose | 1.10 |
| Zinc citrate | 1.00 |
| Titanium(IV) oxide | 0.50 |
| Water (deionized) | 4.50 |
| Sodium lauryl sulfate (SLS) | 1.50 |
| Aroma mixture | 1.00 |
| SymDiol ® 68 (1,2-hexanediol. Caprylyl glycol) | 0.25 |
| Aroma mixture 4 | 0.10 |

Example 3

Mouthwash (amounts as % by weight)

| COMPONENTS | AMOUNT |
| --- | --- |
| Ethyl alcohol | 10.00 |
| Cremophor CO 40 (PEG 40 hydrogenated castor oil) | 1.00 |
| Aroma mixture | 0.25 |
| Water (deionized) | to 100.00 |
| Sorbitol 70% | 5.00 |
| Sodium saccharin 450 | 0.07 |
| Sodium fluoride | 0.18 |
| Benzoic acid | 0.12 |
| Aroma mixture 3 | 0.30 |

Example 4

Dental gel (amounts as % by weight)

| COMPONENTS | AMOUNT |
| --- | --- |
| Na carboxymethylcellulose | 0.40 |
| Sorbitol 70%. in water | 72.00 |
| Polyethylene glycol (PEG) 1500 | 3.00 |
| Na saccharinate | 0.07 |
| Na fluoride | 0.24 |
| Aroma mixture | 1.00 |
| Abrasive silica | 11.00 |
| Thickening silica | 6.00 |
| Sodium dodecyl sulfate (SDS) | 1.40 |
| Dist. water | to 100 |
| p-Hydroxybenzoic acid (PHB) ethyl ester | 0.15 |
| Aroma mixture 4 | 0.20 |

Example 5

Anti-plaque tooth cream (amounts as % by weight)

| COMPONENTS | AMOUNT |
| --- | --- |
| Carrageenan | 0.90 |
| Glycerol | 15.00 |
| Sorbitol 70%. in water | 25.00 |
| PEG 1000 | 3.00 |
| Na fluoride | 0.24 |
| Tetrapotassium diphosphate | 4.50 |
| Tetrasodium diphosphate | 1.50 |
| Na saccharinate | 0.40 |
| Precipitated silica | 20.00 |
| Titanium dioxide | 1.00 |
| Triclosan | 0.30 |
| Spearmint flavor (comprising 60 wt. % l-carvone and 25 wt. % l-menthol) | 1.00 |
| Sodium dodecyl sulfate | 1.30 |
| Dist. water | to 100 |
| Benzyl alcohol | 0.50 |
| Aroma mixture 3 | 0.25 |

Example 6

Tooth cream for sensitive teeth (amounts as % by weight)

| COMPONENTS | AMOUNT |
| --- | --- |
| Na carboxymethylcellulose | 0.70 |
| Xanthan gum | 0.50 |
| Glycerol | 15.00 |
| Sorbitol 70%. in water | 12.00 |
| Potassium nitrate | 5.00 |
| Sodium monofluorophosphate | 0.80 |
| Na saccharinate | 0.20 |
| Aroma mixture | 1.00 |
| Ca carbonate | 35.00 |
| Silicon dioxide | 1.00 |
| Sodium dodecyl sulfate (SDS) | 1.50 |
| Dist. water | to 100 |
| PHB methyl ester and PHB propyl ester | 0.20 |
| Aroma mixture 4 | 0.50 |

Example 7

Tooth cream and mouthwash 2:1 (amounts as % by weight)

| COMPONENTS | AMOUNT |
| --- | --- |
| Sorbitol | 40.00 |
| Glycerol | 20.00 |
| Ethanol | 5.00 |
| Water | to 100 |
| Na monofluorophosphate | 0.75 |
| Saccharin | 0.20 |
| Sident 9 (abrasive silicon dioxide) | 20.00 |
| Sident 22 S (thickening silicon dioxide) | 2.00 |
| Sodium carboxymethylcellulose | 0.30 |
| Sodium lauryl sulfate (SDS) | 1.20 |
| Color (suspension. 1% in water) C.I. Pigment Blue 15 | 0.50 |
| Aroma mixture | 0.90 |
| Solbrol M. sodium salt (methylparaben. sodium salt) | 0.20 |
| Aroma mixture 3 | 0.30 |

Example 8

Mouthwash with fluoride (amounts as % by weight)

| COMPONENTS | AMOUNT |
| --- | --- |
| Ethanol | 7.00 |
| Glycerol | 12.00 |
| Na fluoride | 0.05 |
| Pluronic F-127 ® (BASF, surface-active substance) | 1.40 |
| Na phosphate buffer pH 7.0 | 1.10 |
| Na saccharinate | 0.10 |
| Aroma mixture | 0.15 |
| Chlorhexidine digluconate | 0.2 |
| Dist. water | to 100 |
| Sorbic acid | 0.20 |
| Aroma mixture 4 | 0.30 |

Example 9

Sugar-free chewing gum (amounts as % by weight)

| COMPONENTS | AMOUNT |
| --- | --- |
| Chewing gum base | 30.00 |
| Sorbitol. powder | to 100 |
| Palatinite | 9.50 |
| Xylitol | 2.00 |
| Mannitol | 3.00 |
| Aspartame | 0.10 |
| Acesulfame K | 0.10 |
| Emulgum/emulsifier | 0.30 |
| Sorbitol 70%. in water | 14.00 |
| Glycerol | 1.00 |
| Aroma mixture | 1.50 |
| Aroma mixture 3 | 0.20 |

The invention claimed is:

1. A preparation for oral ingestion, comprising at least one aroma preparation comprising:
   (a) a compound selected from eugenol, an essential oil containing eugenol, and a combination of eugenol and an essential oil containing eugenol; and
   (b) a mixture of menthol and menthyl acetate at a weight ratio of 80:20 to 20:80 menthol to menthyl acetate,
   wherein components (a) and (b) are present in a weight ratio of from 80:20 to 99:1.

2. The preparation for oral ingestion, according to claim 1, wherein the preparation for oral ingestion is of a type selected from foodstuffs, pharmaceutical preparations, oral and tooth care agents.

3. The preparation for oral ingestion, according to claim 2, wherein the foodstuffs are selected from hard caramels, chewing sweets, and chewing gums.

4. The preparation for oral ingestion, according to claim 2, wherein the pharmaceutical preparations are selected from cold relief syrups, cold relief sprays, and cold relief sweets.

5. The preparation for oral ingestion, according to claim 2, wherein the oral and tooth care agents are selected from toothpastes, mouthwashes, and medicinal chewing gums.

6. The preparation for oral ingestion, according to claim 1, wherein the at least one aroma preparation is present in an amount of from approximately 0.5 to approximately 5% by weight—based on the final preparation.

7. A method of enhancing a warm-spicy taste and reducing a burning, painful taste of an essential oil comprising the preparation of claim 1.

* * * * *